United States Patent [19]

Wagner et al.

[11] Patent Number: 4,716,252

[45] Date of Patent: Dec. 29, 1987

[54] PROCESS FOR THE PREPARATION OF BIS-HYDROXYPHENYL-N-ALKANES, NEW BIS-HYDROXYPHENYL-N-ALKANES AND NEW ALKANEDIONES

[75] Inventors: Rudolf Wagner, Cologne; Kurt Halcour, Leverkusen; Hans-Rudolf Dicke; Volker Eckhardt, both of Krefeld, all of Fed. Rep. of Germany

[73] Assignee: Bayer Aktiengesellschaft, Leverkusen, Fed. Rep. of Germany

[21] Appl. No.: 891,491

[22] Filed: Jul. 28, 1986

[30] Foreign Application Priority Data

Aug. 2, 1985 [DE] Fed. Rep. of Germany ....... 3527862

[51] Int. Cl.$^4$ ...................... C07C 39/16; C07C 37/00
[52] U.S. Cl. ...................................... 568/729; 568/799
[58] Field of Search ........................ 568/729, 799, 325

[56] References Cited

U.S. PATENT DOCUMENTS 3,567,787  3/1971  Hennis ................................. 568/729
3,956,402  5/1976  Schellenbaum ..................... 568/729

FOREIGN PATENT DOCUMENTS 4216  12/1969  Japan ................................. 568/325

OTHER PUBLICATIONS

Todd, "Organic Reactions", vol. IV, pp. 378+ (1948).

Primary Examiner—Werren B. Lone
Attorney, Agent, or Firm—Sprung Horn Kramer & Woods

[57] ABSTRACT

Bis-hydroxyphenyl-n-alkanes are prepared by contacting dicarboxylic acids or dicarboxylic acid derivatives with fluorine-containing organic sulphonic acids, where appropriate with the addition of a phenolic compound, and converting the alkanediones, which are thus obtainable, into bis-hydroxyphenyl-n-alkanes by hydrogenation and, where appropriate, an additional ether cleavage. The invention also relates to new bis-hydroxyphenyl-n-alkanes and to new alkanediones.

5 Claims, No Drawings

PROCESS FOR THE PREPARATION OF BIS-HYDROXYPHENYL-N-ALKANES, NEW BIS-HYDROXYPHENYL-N-ALKANES AND NEW ALKANEDIONES

The present invention relates to a process for the preparation of bis-hydroxyphenyl-n-alkanes by contacting dicarboxylic acids or dicarboxylic acid derivatives with fluorine-containing organic sulphonic acids, where appropriate with the addition of a phenolic compound, and converting the alkanediones, which are thus obtainable, into bis-hydroxyphenyl-n-alkanes by hydrogenation and, where appropriate, by an additional ether cleavage.

The preparation of a few particular alkanediones has already been disclosed in Journal Indian Chem. Soc. 46, No. 4, 351–357 and 46, No. 8, 743–746 (1969). This entails reaction of dichlorides of pimelic, suberic, azelaic or sebacic acid with phenol or anisole with the addition of aluminum chloride. However, the yields and selectivities achieved by this method are unsatisfactory. Furthermore, the aluminum chloride which is used cannot be recovered and reused.

The preparation of certain bis-hydroxyphenyl-n-alkanes has also already been disclosed (see Zh. Organ. Khim. 1 (9), 1602–1604 (1965) and C.A. 64, 623 f). This entails reaction of acid chlorides of adipic, suberic or sebacic acid with anisole and aluminum chloride, subsequent reduction of the resulting diones with hydrazine, and subsequently carrying out demethylation thereon with hydriodic acid. This process has the same disadvantages as that described above.

A process for the preparation of bis-hydroxyphenyl-n-alkanes of the formula (I)

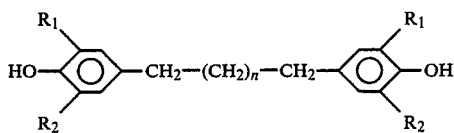

in which n represents an integer in the range from 0 to 10, and
$R_1$ and $R_2$, independently of one another, represent hydrogen, $C_1$- to $C_{12}$-alkyl, $C_1$- to $C_4$-alkoxy and/or halogen, has now been found, which is characterized in that dicarboxylic acids or dicarboxylic acid derivatives of the formula (II)

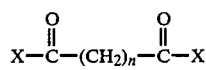

in which n has the abovementioned meaning, and
X represents
(a) OH or halogen, or both X's form, together with the molecular moiety $-CO-(CH_2)_n-CO-$, the corresponding cyclic or polymeric dicarboxylic anhydride, or represents
(b) the radical (III)

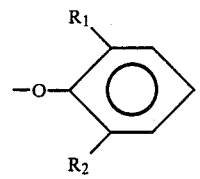

in which $R_1$ and $R_2$ have the abovementioned meaning, are contacted with fluorine-containing organic sulphonic acids, with the addition, in the case where X=(a), of a phenolic compound of the formula (IV)

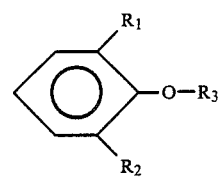

in which $R_1$ and $R_2$ have the abovementioned meaning, and
$R_3$ represents hydrogen or $C_1$- to $C_{12}$-alkyl, and thus alkanediones of the formula (V) are obtained

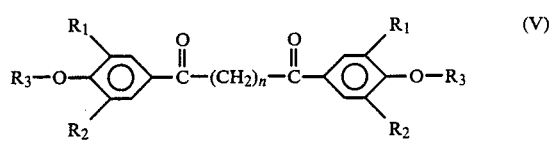

in which n, $R_1$, $R_2$ and $R_3$ have the above mentioned meaning, which are converted by hydrogenation, and in the case where $R_3=C_1$- to $C_{12}$-alkyl by an additional ether cleavage, into the bis-hydroxyphenyl-n-alkanes of the formula (I).

In the formulae (I), (II) and (V), n preferably represents an integer in the range from 6 to 10. In the formulae (I), (II), (IV) and (V), $R_1$ and $R_2$ independently of one another preferably represent hydrogen, $C_1$- to $C_6$-alkyl, fluorine, chlorine and/or bromine. $R_1$ and $R_2$ are particularly preferably identical and represent hydrogen, methyl, ethyl or chlorine. $R_1$ and $R_2$ very particularly preferably represent hydrogen. In the formula (II), X particularly preferably represents OH or halogen. In the formulae (IV) and (V), $R_3$ preferably represents hydrogen or $C_1$- to $C_4$-alkyl, and particularly preferably represents hydrogen. X, $R_1$ and $R_2$ can, when each is halogen, denote fluorine, chlorine, bromine and/or iodine. Of these, fluorine, chlorine and bromine are preferred, and chlorine is particularly preferred.

The compounds of the formula (II) which are to be used in the process according to the invention can be, for example, saturated aliphatic dicarboxylic acids having 2 to 12 C atoms, the corresponding acid halides and the corresponding acid anhydrides. Examples of dicarboxylic acids of this type are oxalic, malonic, succinic, glutaric, adipic, pimelic, suberic, azelaic, sebacic, undecanedicarboxylic and dodecanedicarboxylic acid. Examples of acid halides are the difluorides, dichlorides, dibromides and diiodides of these above-mentioned acids, in particular the dichlorides. Examples of acid anhydrides are the cylic succinic anhydride, the cyclic glutaric anhydride and the polymeric adipic anhydride. All these compounds are commercial products or can be prepared in a straightforward manner by customary methods.

The compounds of the formula (II) which can be used in the process according to the invention can also be the diphenyl esters of the dicarboxylic acids, which can be substituted in the phenyl moiety in the 2- and/or 6-position by $C_1$- to $C_{12}$-alkyl, $C_1$- to $C_4$-alkoxy and/or halogen. Examples of compounds of this type are diphenyl glutarate, diphenyl adipate, diphenyl suberate, diphenyl azelate, diphenyl sebacate, diphenyl dodecanedicarboxylate and bis-(2,6-dimethylphenyl) sebacate. Diphenyl esters of this type can be obtained by, for example, reaction of diphenyl carbonates of the formula (VIII)

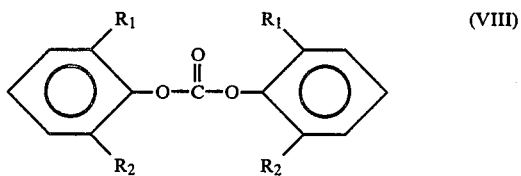

in which
$R_1$ and $R_2$ have the abovementioned meaning, or by reaction of phenols of the formula (IV), with $R_3=H$, in each case with dicarboxylic acids or dicarboxylic acid derivatives of the formula (II), with $X=(a)$, in the presence of basic catalysts.

If the intention is to use in the process according to the invention compounds of the formula (II) with $X=(a)$, the addition of phenolic compounds of the formula (IV) is necessary. Examples of compounds of the formula (IV) are phenol, methylphenol, 2,6-dimethylphenol, 2-ethylphenol, 2,6-diethylphenol, 2-chlorophenol, 2,6-dichlorophenol, phenyl methyl ether, phenyl ethyl ether, 2,6-dimethylphenyl methyl ether and phenyl isopropyl ether.

It is possible to add, for example, 1.5 to 2.5 mol of a compound of the formula (IV) relative to one mol of a compound of the formula (II) with $X=(a)$. This amount is preferably 1.8 to 2.2 mol, particularly preferably 1.9 to 2.1 mol.

It is an essential feature of the process according to the invention that the compounds of the formula (II) are contacted with fluorine-containing organic sulphonic acids, with, in the cases which are described, the addition of compounds of the formula (IV). The fluorine-containing organic sulphonic acids can be, for example, alkanesulphonic acids which are completely or partially substituted by fluorine atoms, aromatic sulphonic acids which are completely substituted by fluorine, or appropriate fluorine-containing sulphonic acid radicals which are bonded to a resin matrix. Organic sulphonic acids which contain 1 to 3 fluorine atoms on the C atom which is adjacent to the sulphonic acid group are preferred. Perfluorinated alkanesulphonic acids having, for example, 2 to 8 C atoms, and resin matrices containing appropriate sulphonic acid radicals, in particular trifluoromethanesulphonic acid, perfluorobutanesulphonic acid, perfluorooctanesulphonic acid and ion exchangers which are commercially available under the name Nafion ®, are particularly preferred.

The fluorine-containing organic sulphonic acids can be used in, for example, amounts of 1 to 10 mol per mol of compound of the formula (II). This amount is preferably 1.5 to 4.5 mol. When compounds of the formula (II) with $X=(a)$ are used, then preferably 3.5 to 4.5 mol, particularly preferably 3.9 to 4.1 mol, of fluorine-containing organic sulphonic acids are used per mol of the compound of the formula (II). When compounds of the formula (II) with $X=(b)$ are used, then preferably 1.5 to 2.5 mol, particularly preferably 1.9 to 2.1 mol, of fluorine-containing organic sulphonic acid are used per mol of the compound of the formula (II).

The temperatures which are maintained for the formation of the alkanediones of the formula (V) can be, for example, those in the range from 20° to 120° C. The temperature for this is preferably maintained in the range from 20° to 60° C. This reaction is normally carried out under atmospheric pressure. However, it is also possible to carry it out under reduced or elevated pressure, for example in the range from 0.5 to 5 bar. The presence of solvents is not necessary but is possible and sometimes advantageous. Examples of suitable solvents are those which are aprotic and stable to acids. Chlorinated saturated hydrocarbons, such as methylene chloride, chloroform and dichloroethane, are preferred.

The holdup times for the formation of the alkanediones of the formula (V) can be varied within wide limits. Examples of suitable holdup times are in the range from 1 minute to 2 hours. Holdup times in the range from 20 to 60 minutes are preferred.

The working up of the reaction mixture which is subsequently obtained can be carried out, for example, in such a manner that any solvent which is present is first removed, for example by distillation, where appropriate under reduced pressure. It is a particular advantage of the process according to the invention that the fluorine-containing organic sulphonic acids can be recovered and reused. For this purpose, it is possible, for example, to add water to the reaction mixture from which, where appropriate, the solvent has been removed. This results in the reaction product (the compound of the formula (V)) precipitating out. It can be filtered off and, if desired, additionally purified by, for example, recrystallization. A recrystallization of this type can be carried out with, for example, alcohols, alcohol/water mixtures or aromatic hydrocarbons. Ethanol, ethanol/water mixtures and toluene are preferred for this. The aqueous filtrate contains the fluorine-containing organic sulphonic acid used. To recover this, it is possible, where appropriate after a wash with an organic solvent, for example ethyl acetate, to add a base which is able to form insoluble salts, for example an alkali metal or alkaline earth metal hydroxide, in particular potassium, calcium or barium hydroxide. It is then possible to add highly concentrated, for example 100% strength, sulphuric acid to the salt of the fluorine-containing organic sulphonic acid, preferably after drying, and to obtain from this mixture the fluorine-containing organic sulphonic acid by distillation under reduced pressure, and to reuse it. Recovery rates of, for example, more than 95% may be achieved with this procedure.

The removal of a fluorine-containing organic sulphonic acid which is bonded to a resin matrix can be effected simply by filtration of the reaction mixture. The acid can be reused, where appropriate after washing and drying. The compound of the formula (V) can then be isolated from the filtrate as described above.

The hydrogenation of the compounds of the formula (V) which have been prepared according to the invention to give the bis-hydroxyphenyl-n-alkanes of the formula (I) can be effected in a manner known per se. It is possible, for example, to dissolve the compound of the formula (V) in a solvent, for example tetrahydrofuran and dioxane being suitable, and to carry out catalytic hydrogenation at 60° to 150° C., preferably 80° to 120° C., under a partial pressure of hydrogen of 5 to 50 bar, preferably 15 to 25 bar, and with a holdup time of 0.1 to 4 hours, preferably 0.5 to 2 hours. Suitable catalysts are those, with or without support, which are known to facilitate selective hydrogenation of $>C=O$ groups to $>CH_2$ groups. If desired, it is also possible to use catalysts which (co)hydrogenate the aromatic rings. It is then possible to obtain cyclohexane derivatives derived from the compounds of the formula (I). Catalysts containing nickel or palladium are preferably used, in particular those containing palladium. The hydrogenation product can be obtained from the reaction mixture obtained after the hydrogenation by, for example, removal of the catalyst by filtration and of the solvent by distillation. The remaining hydrogenation product can be purified where appropriate by recrystallisation, for example from aromatic hydrocarbons. In those cases in which either compounds of the formula (II) with X=(b) or compounds of the formula (II) with X=(a) have been used in combination with com-pounds of the formula (IV) with $R_3$=hydrogen, then the hydrogenation product is the desired bis-hydroxy-phenyl-n-alkane of the formula (I). In those cases in which compounds of the formula (II) with X=(a) have been used in combination with compounds of the formula (IV) with $R_3=C_1$- to $C_{12}$-alkyl, the hydrogenation product is an etherified bis-hydroxyphenyl-n-alkane (compare formula (I), but $R_3O$ groups in place of HO groups). Ethers of this type have to be subjected to an additional ether cleavage in order to obtain the desired bis-hydroxyphenyl-n-alkanes of the formula (I).

An ether cleavage of this type can be carried out in a manner known per se, for example with the addition of acetic acid and hydriodic acid at 40° to 100° C. and holdup times of 0.5 to 2 hours, the corresponding alkyl iodide being eliminated. The compounds of the formula (I) which are thus obtained can, where appropriate, additionally be recrystallized for example from aromatic hydrocarbons.

It is extremely surprising that, using the fluorine-containing organic sulphonic acids which are to be used according to the invention, it is possible to obtain compounds of the formula (I) in higher yields and with better selectivities than with the known use of aluminium chloride. It is furthermore worthy of note that the acids which are to be used according to the invention can, in contrast to aluminum chloride, be recovered and reused, which makes the process according to the invention especially environmentally acceptable and economic. It is furthermore surprising that the fluorine-containing organic sulphonic acids exhibit good para selectivity, that is to say products of the formula (I) in which the phenolic OH group and the $CH_2$ chain are located in the para-position on the particular aromatic ring are selectively obtained. From the fact that when compounds of the formula (II) with X=(b) are used the point of linkage of the phenolic molecular moiety with the remainder of the molecule is changed, it is evident that the phenolic molecular moiety is mobile under the reaction conditions of the process according to the invention (see the following reaction diagram)

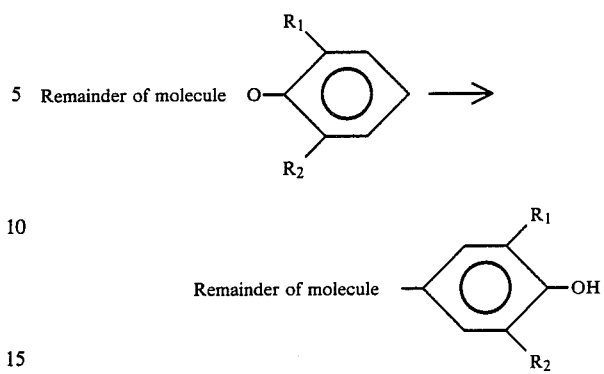

and thus good para selectivity was not to be expected.

The present invention also relates to new alkanediones of the formula (IX)

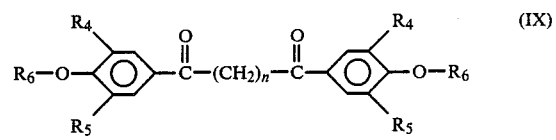

in which n represents an integer in the range from 0 to 10, $R_4$ and $R_5$, independently of one another, represent $C_1$- to $C_{12}$-alkyl, $C_1$- to $C_4$-alkoxy and/or halogen, and $R_6$ represents hydrogen or $C_1$- to $C_{12}$-alkyl.

The new alkanediones of the formula (IX) which are preferred are those in which n represents 4, 6, 8 or 10, $R_4$ and $R_5$, independently of one another, each represent a $C_1$- to $C_4$-alkyl radical and $R_6$ represents hydrogen.

These new alkanediones can be prepared as described above and can be used as intermediates for the preparation of bis-hydroxyphenyl-n-alkanes of the formula (I).

The present invention also relates to new bis-hydroxyphenyl-n-alkanes of the formula (X)

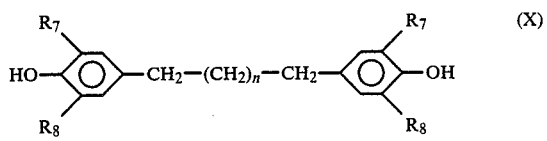

in which n represents an integer in the range from 0 to 10, and $R_7$ and $R_8$, independently of one another, represent $C_1$- to $C_{12}$-alkyl, $C_1$- to $C_4$-alkoxy and/or halogen.

The new bis-hydroxyphenyl-n-alkanes of the formula (X) which are preferred are those in which n represents 4, 6, 8 or 10, and $R_7$ and $R_8$, independently of one another, each represent hydrogen or methyl.

These new bis-hydroxyphenyl-n-alkanes can be prepared as described above.

The known and new bis-hydroxyphenyl-n-alkanes of the formula (I) which can be prepared according to the invention can be used as starting materials for the preparation of dyestuffs, active compounds and polycondensates, for example polyesters and polyethers. Furthermore, these compounds have importance as additives for the stabilization of thermoplastic materials, for example those described in DE-OS (German Published Specification) No. 3,502,378.

The examples which follow illustrate the present invention without restricting it in any way.

EXAMPLES

Example 1

17.4 g (0.1 mol) of suberic acid, 23.5 g (0.25 mol) of phenol and 120 g (0.4 mol) of perfluorobutanesulphonic acid were contacted at 80° C., with exclusion of moisture, and stirred for 2 hours. The reaction mixture was then poured into 500 ml of water, and the resulting precipitate was filtered off. The residue was recrystallized from 500 ml of ethanol. 28 g (85% of theory) of 1,8-bis-(4-hydroxyphenyl)-1,8-octanedione were obtained with a melting point of 196° to 198° C. (decomposition).

Example 2

The process was carried out as described in Example 1, but 20.2 g (0.1 mol) of sebacic acid were used in place of suberic acid. 29 g (82% of theory) of 1,10-bis-(4-hydroxyphenyl)-1,10-decanedione were obtained with a melting point of 193° to 194° C. (decomposition).

Example 3

The process was carried out as described in Example 1, but 23 g (0.1 mol) of dodecanedicarboxylic acid were used in place of suberic acid. 34 g (89% of theory) of 1,12-bis-(4-hydroxyphenyl)-1,12-dodecanedione were obtained with a melting point of 177° to 181° C. (decomposition).

Example 4

The process was carried out as described in Example 1, but 23.9 g (0.1 mol) of sebacoyl dichloride were used in place of suberic acid. 30 g (85% of theory) of 1,10-bis-(4-hydroxyphenyl)-1,10-decanedione were obtained with a melting point of 193° to 194° C. (decomposition).

Example 5

The process was carried out as described in Example 1, but 30.5 g (0.25 mol) of 2,6-dimethylphenol were used in place of phenol. 37 g (90% of theory) of 1,10-bis-(4-hydroxy-2,6-dimethylphenyl)-1,10-decanedione were obtained with a melting point of 128° to 130° C. (decomposition).

Example 6

The process was carried out as decribed in Example 1 but 18.4 g (0.1 mol) of sebacic anhydride were used in place of suberic acid. 32 g (91% of theory) of 1,10-bis-(4-hydroxyphenyl)-1,10-decanedione were obtained with a melting point of 193° to 194° C. (decomposition).

Example 7

52 g (0.2 mol) of diphenyl glutarate, 120 g (0.4 mol) of perfluorobutanesulphonic acid and 200 ml of 1,2-dichloroethane were mixed, with exclusion of moisture, and stirred at room temperature for 2 hours. The methylene chloride was then evaporated off in vacuo at a bath temperature of 30° C. The red residue was poured into 500 ml of water, and the precipitate was filtered off. 1 g of the product thus obtained was worked up by column chromatography on silica gel using 15% ethyl acetate in hexane. 1,5-Bis-(4-hydroxyphenyl)-1,5-pentanedione (0.2 g) was obtained as a red oil in the component which was eluted 2nd, and was characterized by mass spectroscopy (M284) and by $^1$H-NMR spectroscopy (in d$_6$-DMSO $\delta$7.86 (4H, d),$\delta$6.87 (4H, d),$\delta$3.04 (4H, t),$\delta$2.15 (2H, m),$\delta$8.7 (2H, s)). A total yield of 17 g (30% of theory) of 1,5-bis(4-hydroxyphenyl)-1,5-pentanedione was obtained with a melting point of 158° to 163° C. (decomposition).

Example 8

A reaction was carried out as described in Example 7, but 54.8 g (0.2 mol) of diphenyl adipate were used in place of diphenyl glutarate. After removal of the solvent, the reaction mixture was poured into 500 ml of water, and the yellow precipitate which formed was filtered off. The residue from filtration was recrystallized from ethanol/water. 33 g (60% of theory) of 1,6-bis-(4-hydroxyphenyl)-1,6-hexanedione were obtained as a pale yellow solid with a melting point of 232°-238° C. (decomposition).

Example 9

The process was carried out as in Example 8, but 65.2 g (0.2 mol) of diphenyl suberate were used in place of diphenyl adipate, and the mixture was stirred at 80° C. (instead of room temperature). 54.1 g (83% of theory) of 1,8-bis-(4-hydroxyphenyl)-1,8-octanedione were obtained as a pale yellow solid with a melting point of 196° to 198° C.

Example 10

The process was carried out as described in Example 8, but 68 g (0.2 mol) of diphenyl azelate were used in place of diphenyl adipate, and toluene was used to recrystallize the product. 54.4 g (80% of theory) of 1,9-bis-(4-hydroxyphenyl)-1,9-nonanedione were obtained as a pale yellow solid with a melting point of 130° to 137° C. (decomposition).

Example 11

The process was carried out as described in Example 9, but 70.8 g (0.2 mol) of diphenyl sebacate were used in place of diphenyl suberate. 53.8 g (76% of theory) of 1,10-bis-(4-hydroxyphenyl)-1,10-decanedione were obtained with a melting point of 193° to 194° C. (decomposition).

Example 12

The process was carried out as described in Example 9, but 76.4 g (0.2 mol) of diphenyl dodecanoate were used in place of diphenyl suberate. 45.8 g (60% of theory) of α,ω-bis-(4-hydroxyphenyl)-α,ω-dodecanedione were obtained as a pale yellow solid with a melting point of 177° to 181° C. (decomposition).

Example 13

An aqueous filtrate obtained in accordance with Example 1 was washed with 100 ml of ethyl acetate and then neutralized with 22.4 g (0.4 mol) of potassium hydroxide dissolved in 100 ml of water. The mixture was then evaporated and dried at 80° C./26 mbar. In this way, 135 g (100% of theory) of potassium perfluorobutanesulphonate were obtained. Then 200 ml of 100% strength sulphuric acid were added to the latter product, and the perfluorobutanesulphonic acid which was thus liberated was removed by distillation at 112° C./7 mbar. In this way, 116.4 g (97% of theory) of perfluorobutanesulphonic acid were recovered. The perfluorobutanesulphonic acid thus recovered was made up to 120 g with 3.6 g of fresh perfluorobutanesulphonic acid and was reused for reaction of sebacic acid and phenol in accordance with the procedure described in Example 2. This resulted in 29 g (82% of theory) of 1,10-bis-(4-hydroxyphenyl)-1,10-decanedione being obtained.

Example 14

In each case, 100 g of dihydroxy diketone were dissolved in 400 ml of dioxane, and 5 g of 5% palladium on charcoal were added. Then hydrogenation was carried out in a stirred autoclave with a capacity of 700 ml, at 100° C. and under a pressure of 20 bar of hydrogen. The catalyst was then removed by filtration, the dioxane was removed by distillation, and the residue was recrystallized from 300 ml of toluene. The dihydroxy diketones which were used, the bis-(4-hydroxyphenyl)-n-alkanes which were obtained, the yields and melting points are shown in Table 1.

TABLE 1

| Dihydroxy diketone used (1,x-bis-(4-hydroxyphenyl)-1,x-y-dione) | Hydrogenation product obtained (1,x-bis-(4-hydroxyphenyl)-n-y) | Yield (g) | (% of theory) | Melting point (°C.) |
| --- | --- | --- | --- | --- |
| x = 6, y = hexane | x = 6, y = hexane | 77 | 85 | 143–144 |
| x = 8, y = octane | x = 8, y = octane | 73 | 80 | 138–139 |
| x = 10, y = decane | x = 10, y = decane | 76 | 83 | 138–139 |
| x = 12, y = dodecane | x = 12, y = dodecane | 70 | 75 | 134–135 |

What is claimed is:

1. A process for the preparation of a bis-hydroxyphenyl-n-alkane of the formula (I)

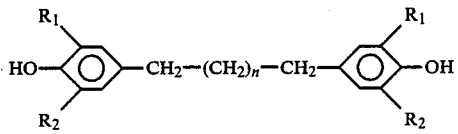

in which
n represents an integer in the range from 0 to 10, and
$R_1$ and $R_2$, independently of one another, represent hydrogen, $C_1$- to $C_{12}$-alkyl, $C_1$- to $C_4$-alkoxy and/or halogen, wherein 1 mol of a dicarboxylic acid or dicarboxylic acid derivative of the formula (II)

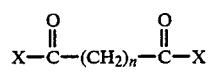

in which
n has the abovementioned meaning, and
X represents
(a) OH or halogen, or both X's form, together with the molecular moiety —CO—$(CH_2)_n$—CO—, the corresponding cyclic or polymeric dicarboxylic anhydride, or represents
(b) the radical (III)

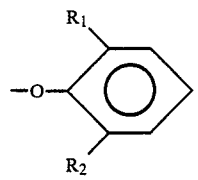

in which
$R_1$ and $R_2$ have the abovementioned meaning, is contacted with 1 to 10 mols of a fluorine-containing organic sulphonic acids, with the addition, in the case where X=(a), of a phenolic compound of the formula (IV)

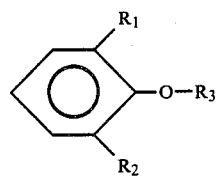

in which
$R_1$ and $R_2$ have the abovementioned meaning, and
$R_3$ represents hydrogen or $C_1$- to $C_{12}$-alkyl, at temperatures in the range from 20° to 120° C., pressures in the range from 0.5 to 5 bar and holdup times in the range from 1 minute to 2 hours to form an alkanedione of the formula (V)

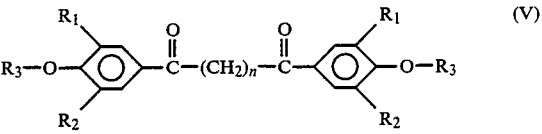

in which
n, $R_1$, $R_2$ and $R_3$ have the abovementioned meaning, which is converted by hydrogenation, and in the case where $R_3$=$C_1$- to $C_{12}$-alkyl by an additional ether cleavage, into a bis-hydroxyphenyl-n-alkanes.

2. A process according to claim 1, wherein
n represents an integer in the range from 6 to 10,
$R_1$ and $R_2$, independently of one another, represent hydrogen, $C_1$- to $C_6$-alkyl, fluorine, chlorine and/or bromine,
$R_3$ represents hydrogen or $C_1$- to $C_4$-alkyl, and
X represents OH or halogen.

3. A process according to claim 1, wherein an alkanesulphonic acid substitued with fluorine atoms, or an appropriate fluorine-containing sulphonic acid radical which is bonded to a resin matrix is used as the fluorine-containing organic sulphonic acid.

4. A process according to claim 3, wherein a perfluorinated alkanesulphonic acid having 2 to 8 C atoms, or resin matrices containing appropriate sulphonic acid radicals, is used.

5. A process according to claim 1, wherein 3.5 to 4.5 mol of fluorine-containing organic sulphonic acid is used for one mol of a compound of the formula (II) with X=(a), and 1.5 to 2.5 mol of fluorine-containing organic sulphonic acid are used for 1 mol of a compound of the formula (II) with X=(b).

* * * * *